US010087141B2

(12) United States Patent
Glaser et al.

(10) Patent No.: US 10,087,141 B2
(45) Date of Patent: Oct. 2, 2018

(54) SYNTHESIS OF [$^{18}$F]-FLUOROALKYL TOSYLATE

(71) Applicant: GE Healthcare Limited, Amersham Place, Buckinghamshire (GB)

(72) Inventors: Matthias Eberhard Glaser, Amersham (GB); Sajinder Luthra, Amersham (GB); Jane Brown, Amersham (GB); Robert James Nairne, Amersham (GB)

(73) Assignee: GE HEALTHCARE LIMITED, Uppsala (SE)

( * ) Notice: Subject to any disclaimer, the term of this patent is extended or adjusted under 35 U.S.C. 154(b) by 0 days.

(21) Appl. No.: 14/910,493

(22) PCT Filed: Aug. 21, 2014

(86) PCT No.: PCT/US2014/052002
§ 371 (c)(1),
(2) Date: Feb. 5, 2016

(87) PCT Pub. No.: WO2015/027012
PCT Pub. Date: Feb. 26, 2015

(65) Prior Publication Data
US 2016/0176807 A1    Jun. 23, 2016

Related U.S. Application Data

(60) Provisional application No. 61/868,766, filed on Aug. 22, 2013.

(51) Int. Cl.
| | |
|---|---|
| *C07B 59/00* | (2006.01) |
| *C07C 303/22* | (2006.01) |
| *C07C 303/30* | (2006.01) |
| *C07C 303/44* | (2006.01) |
| *B01J 19/24* | (2006.01) |

(52) U.S. Cl.
CPC ............ *C07C 303/22* (2013.01); *B01J 19/24* (2013.01); *C07B 59/001* (2013.01); *C07C 303/30* (2013.01); *C07C 303/44* (2013.01); *B01J 2219/24* (2013.01); *C07B 2200/05* (2013.01)

(58) Field of Classification Search
CPC ... C07B 59/001; C07C 303/30; C07C 309/73; C07C 303/44; B01J 19/24
See application file for complete search history.

(56) References Cited

U.S. PATENT DOCUMENTS

| | | | |
|---|---|---|---|
| 9,346,771 B2* | 5/2016 | Horn .................. | A61K 51/0402 |
| 2015/0017093 A1* | 1/2015 | Keiding ............ | A61K 51/0402 |
| | | | 424/1.45 |
| 2015/0175553 A1* | 6/2015 | Wouters .................. | C07B 59/00 |
| | | | 548/327.5 |

FOREIGN PATENT DOCUMENTS

| | | |
|---|---|---|
| EP | 3036209 A1 | 6/2016 |
| WO | 2013/049431 A2 | 4/2013 |
| WO | 2013/053941 A1 | 4/2013 |
| WO | 2015/027012 A1 | 2/2015 |

OTHER PUBLICATIONS

Schoultz et al. "A Fully Automated Radiosynthesis of [18F]Fluoroethyl-Diprenorphine on a Single Module by Use of SPE Cartridges for Preparation of High Quality 2-[18F]Fluoroethyl Tosylate" Molecules 2013, 18, 7271-7278.*
Schoultz et al. Molecules 2013, 18, 7271-7278.*
Of McDonald, P. D. "A Sample Preparation Primer and Guide to Solid Phase Extraction Methods Development" 2001[online]: Waters Co. [retrieved on Aug. 23, 2017]. Retrieved from <http://www.waters.com/webassets/cms/library/docs/wa20300.pdf>.*
Zhang et al. Appl. Rad. Isot. 2002, 57, 335-342.*
International Search Report and Written Opinion regarding International Application No. PCT/US2014/052002, dated Nov. 3, 2014, 6 pages.
Bent Schoultz et al., "A Fully Automated Radiosynthesis of [18-f] Fluoroethyl-Diprenorphine on a Single Module by Use of SPE Cartridges for Preparation of High Quality 2-[18F] Fluoroethyl Tosylate", Molecules, vol. 18, No. 6, Jun. 20, 2013, 8 pages.
Musachio et al., "Radiosyntheses and Reactivities of Novel [18F]2-Fluoroethyl Arylsulfonates", Journal of Labelled compounds and Pharmaceuticals, vol. 48, Issue-10, Jul. 25, 2005, pp. 735-747.
Neal et al., "Improved Synthesis of [18F] Fluoromethyl Tosylate, a Convenient Reagent for Radiofluoromethylations", Journal of Labelled Compounds & Radiopharmaceuticals, vol. 48, 2005, pp. 557-568.
Pascali et al., "Microfluidic Approach for Fast Labeling Optimization and Dose-on-Demand Implementation", Nuclear Medicine and Biology, vol. 37, Issue-5, 2010, pp. 547-555.
Robins et al., "Synthesis and in Vitro Evaluation of (18)F-Labelled S-Fluoroalkyl Diarylguanidines: Novel High-Affinity NMDA Receptor Antagonists for Imaging With PET", Bioorganic & medicinal Chemistry Letters vol. 20, Issue-5, 2010, pp. 1749-1751.
Tang et al., "Fully Automated Synthesis of O-(3-[18F]Fluoropropyl)-L-Tyrosine by Direct Nucleophilic Exchange on a Quaternary 4-Aminopyridinium Resin", Applied Radiation and Isotopes, vol. 58, Issue-6, 2003, pp. 685-689.
Wadsak et al., "18F Fluoroethylations: Different Strategies for the Rapid Translation of 11C-Methylated Radiotracers", Nuclear Medicine and Biology, vol. 34, Issue-8, 2007, pp. 1019-1028.

(Continued)

*Primary Examiner* — Amanda L Aguirre
(74) *Attorney, Agent, or Firm* — Arent Fox LLP

(57) ABSTRACT

[$^{18}$F]-fluoralkyl tosylates are useful building block for the radiosynthesis of a number of small molecules. A method of purifying [$^{18}$F]-fluoroalkyl tosylates using an automated radiosynthesis apparatus (e.g. FASTlab module) is described. A method of purifying [$^{18}$F]-fluoroalky tosylates using a FASTlab module that includes a solid phase extraction (SPE) purification system is described.

14 Claims, 8 Drawing Sheets

(56) References Cited

OTHER PUBLICATIONS

Welch et al., "Handbook of Radiopharmaceuticals: Radiochemistry and Applications", In Chapter: 6, 2002, 862 pages.
International Preliminary Report on Patentability Received for PCT Patent Application No. PCT/US2014/052002, dated Mar. 3, 2016, 6 Pages.
Chinese Search Report Received for Chinese Patent Application No. 201480046453.6, dated Jul. 16, 2017, 8 Pages (6 Pages of Official Copy + 2 Pages of English translation).

* cited by examiner

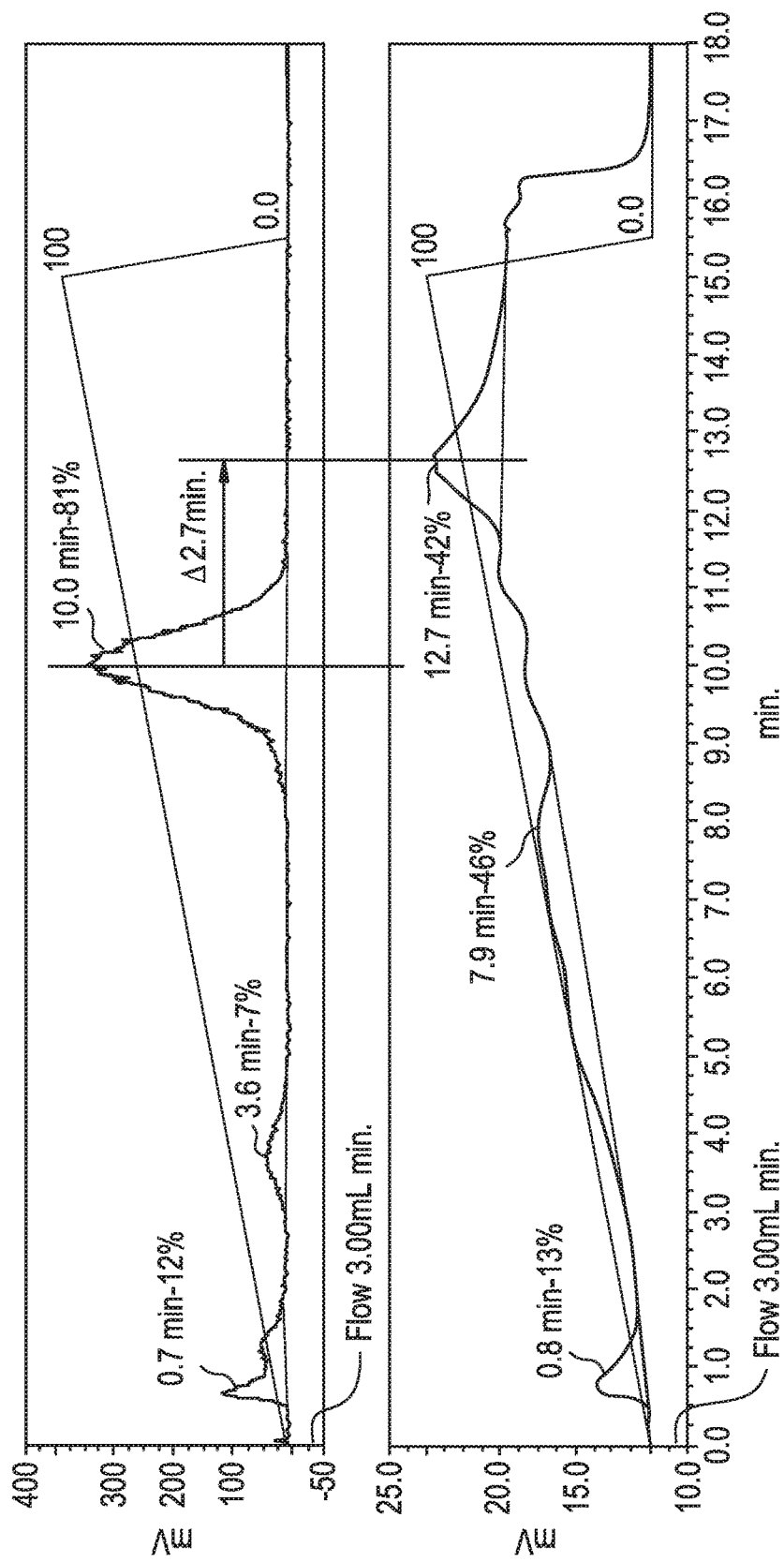

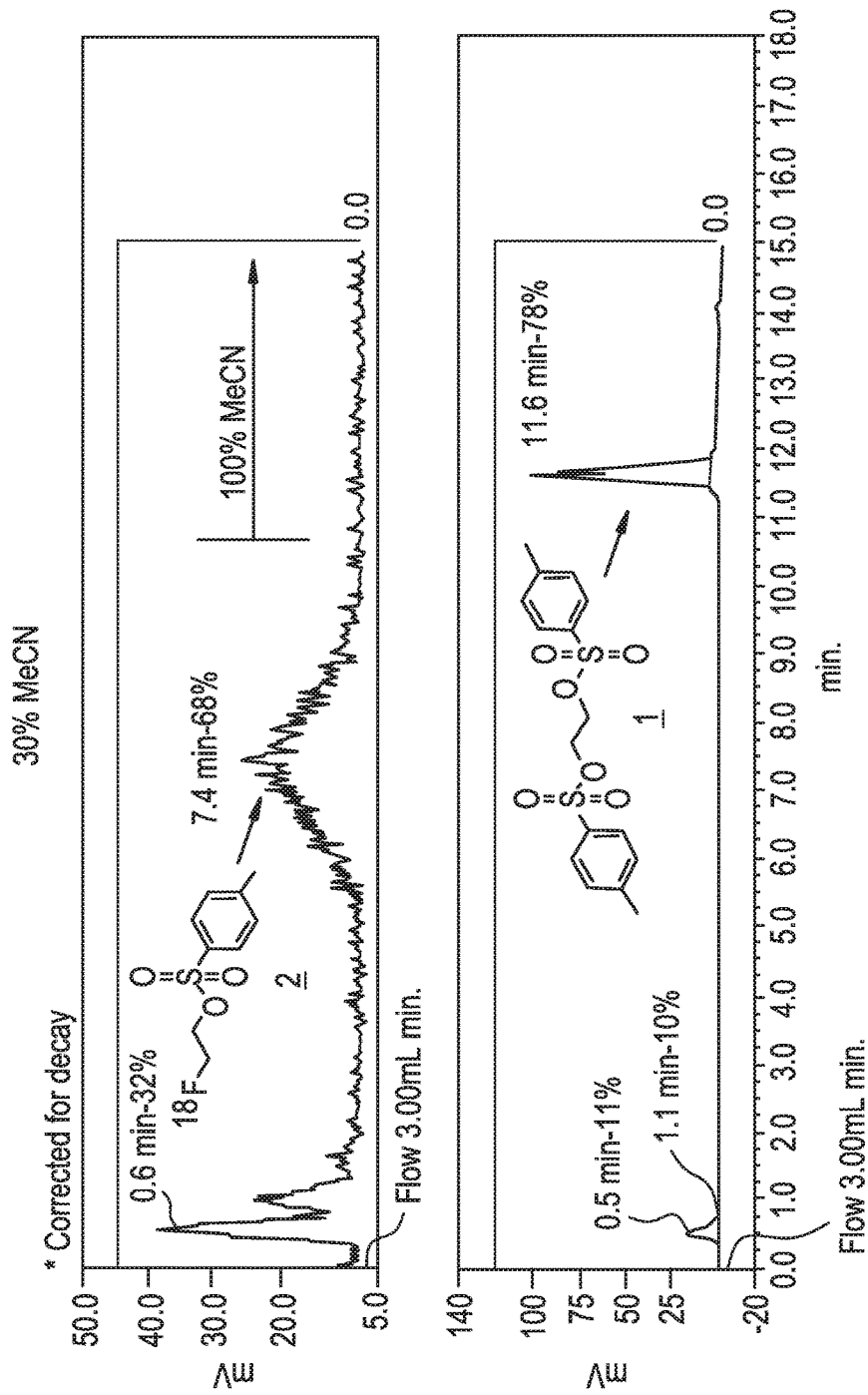

SYNTHESIS OF [$^{18}$F]-FLUOROALKYL TOSYLATE

CROSS REFERENCE TO RELATED APPLICATIONS

This application is a filing under 35 U.S.C. 371 of international application number PCT/US2014/052002, filed Aug. 21, 2014, which claims priority to U.S. application No. 61/868,766, filed Aug. 22, 2013, the entire disclosures of each of which are hereby incorporated by reference.

BACKGROUND

The labelling reagent [$^{18}$F]2-fluoroethyl tosylate is a widely used building block for the radiosynthesis of a number of small molecules (Musachio, J. L., Shah, J. & Pike, V. W. Radiosyntheses and reactivities of novel [$^{18}$F] 2-fluoroethyl arylsulfonates. *J. label. Comp. Radiophann.* 48, 735-747 (2005)). This strategy is generally applied in cases where a one-step approach fails (i.e. the use of a leaving group at the substrate). For a successful alkylation step, it is important to obtain [$^{18}$F]2-fluoroethyl tosylate in high specific radioactivity and/or chemical purity. Currently, product purification can be seen as a challenge in the radiosynthesis of [$^{18}$F]2-fluoroethyl tosylate. The preferred literature methods are based either on preparative HPLC or hexane/diethylether SPE (Wadsak, W. et al. F-18 fluoroethylations: different strategies for the rapid translation of C-11-methylated radiotracers. *Nucl. Med. & Biol.* 34, 1019-1028 (2007)). The present invention described below provides a method of purifying [$^{18}$F]-fluoroalkyl tosylates.

BRIEF DESCRIPTION OF THE FIGURES

FIG. 1D HPLC analysis C30 cartridge eluting with 0-100% MeCN in 15 min, 3 mL/min, in separating 2 from ditosylate precursor 1.
FIG. 2A HPLC analysis tC18 cartridge after loading with crude 2 followed by isocratic elution of 30% MeCN (3 ml/min). The precursor 1 was eluted off with 100% MeCN after 11 min.

SUMMARY OF THE INVENTION

Figure 1A:
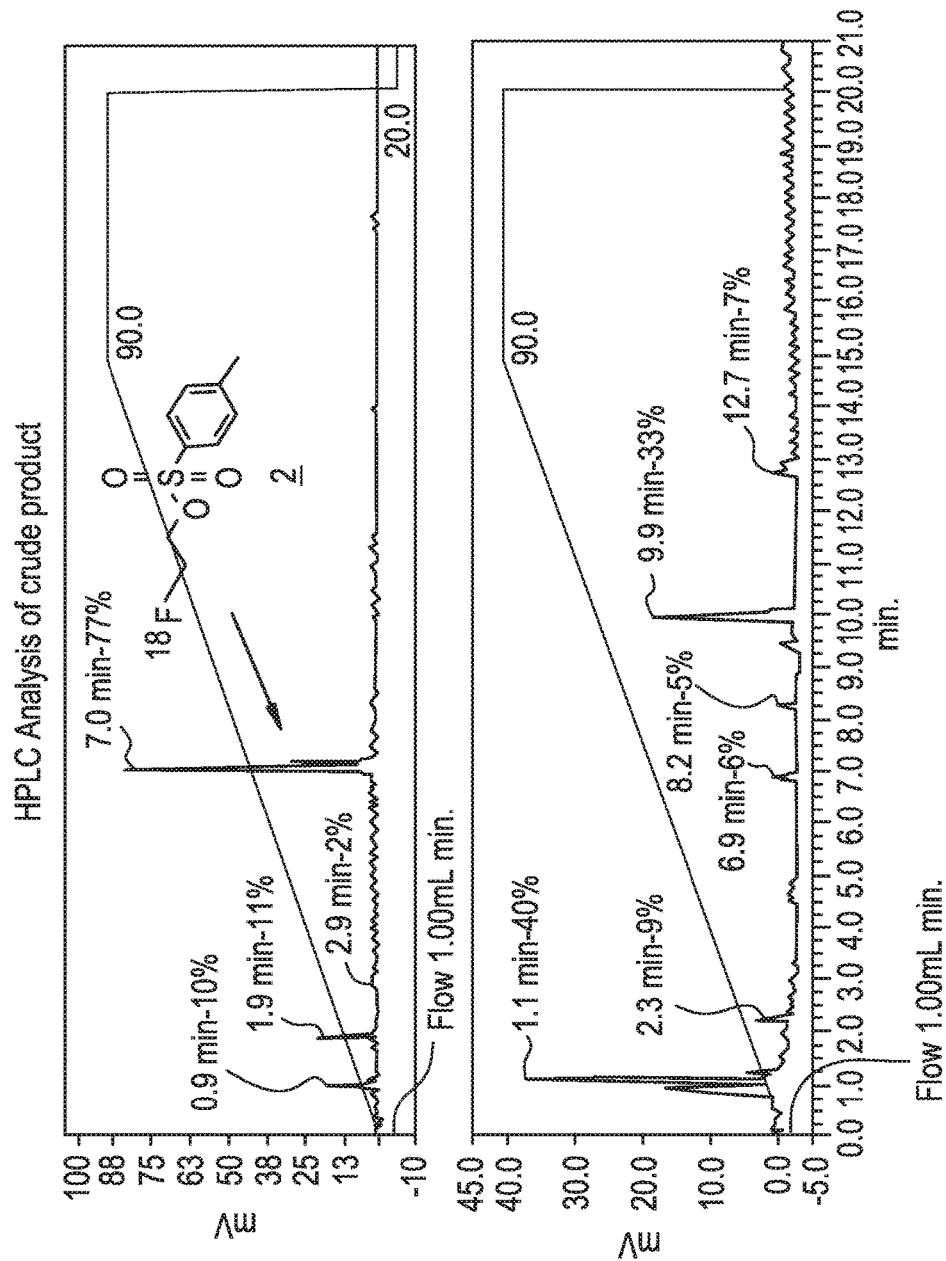
FIG. 1A HPLC analysis of crude product.
Figure 1B:
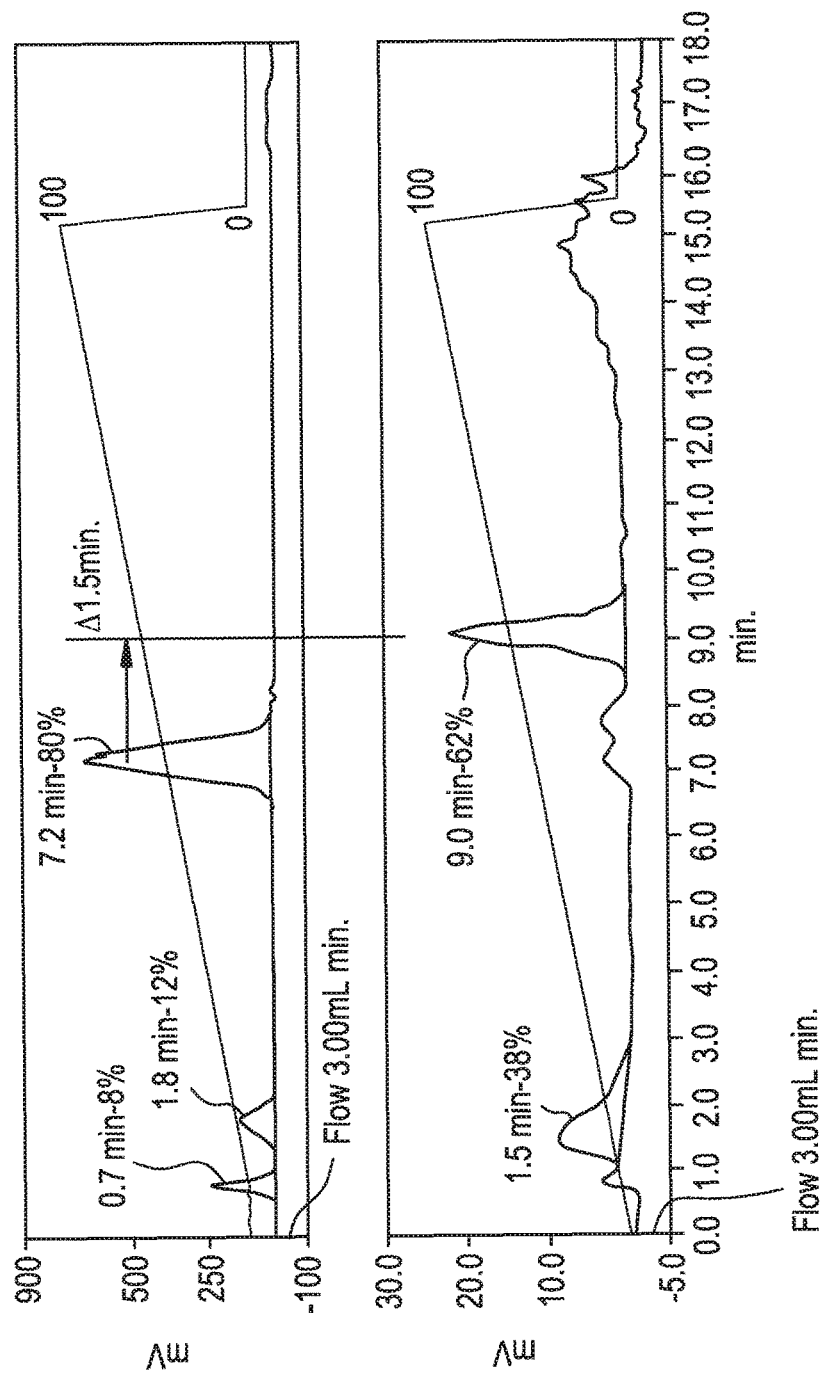
FIG. 1B HPLC analysis tC2 SepPak cartridge eluting with 0-100% MeCN in 15 min, 3 mL/min, in separating 2 from ditosylate precursor 1.
Figure 1C:
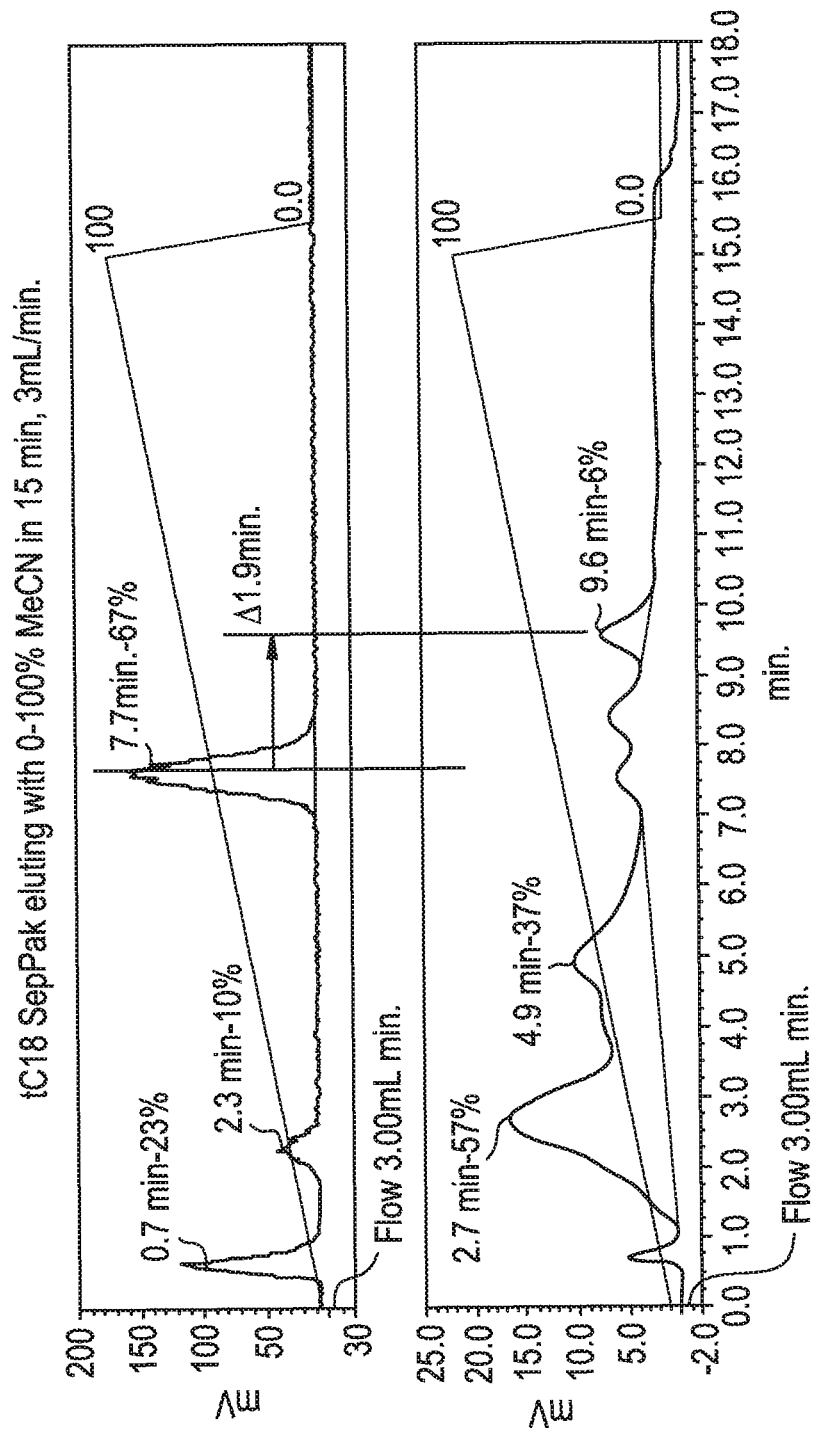
FIG. 1C HPLC analysis tC18 SepPak cartridge eluting with 0-100% MeCN in 15 min, 3 mL/min, in separating 2 from ditosylate precursor 1.
Figure 2B:
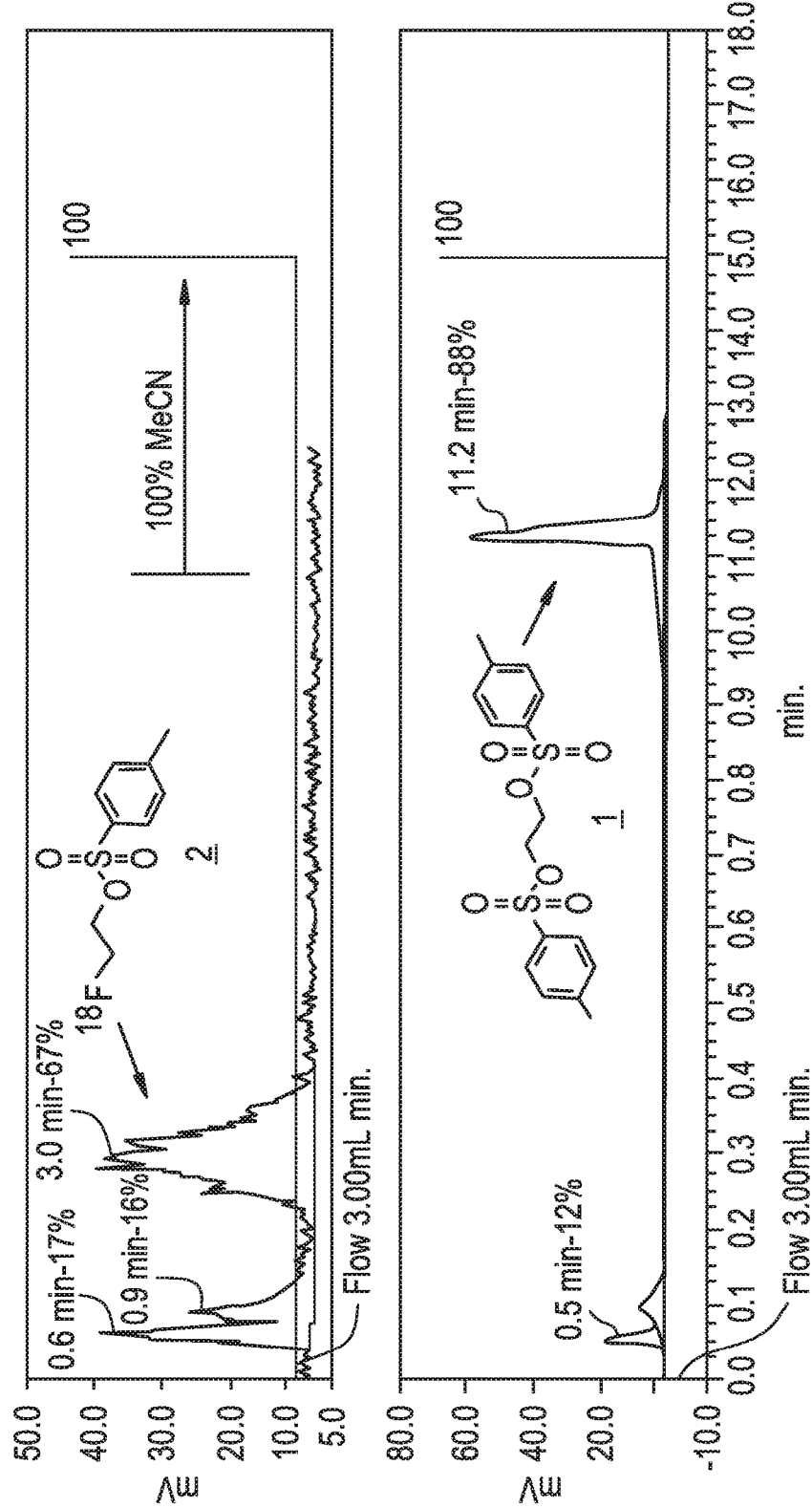
FIG. 2B HPLC analysis tC18 cartridge after loading with crude 2 followed by isocratic elution of 40% MeCN (3 ml/min). The precursor 1 was eluted off with 100% MeCN after 11 min.
Figure 3:
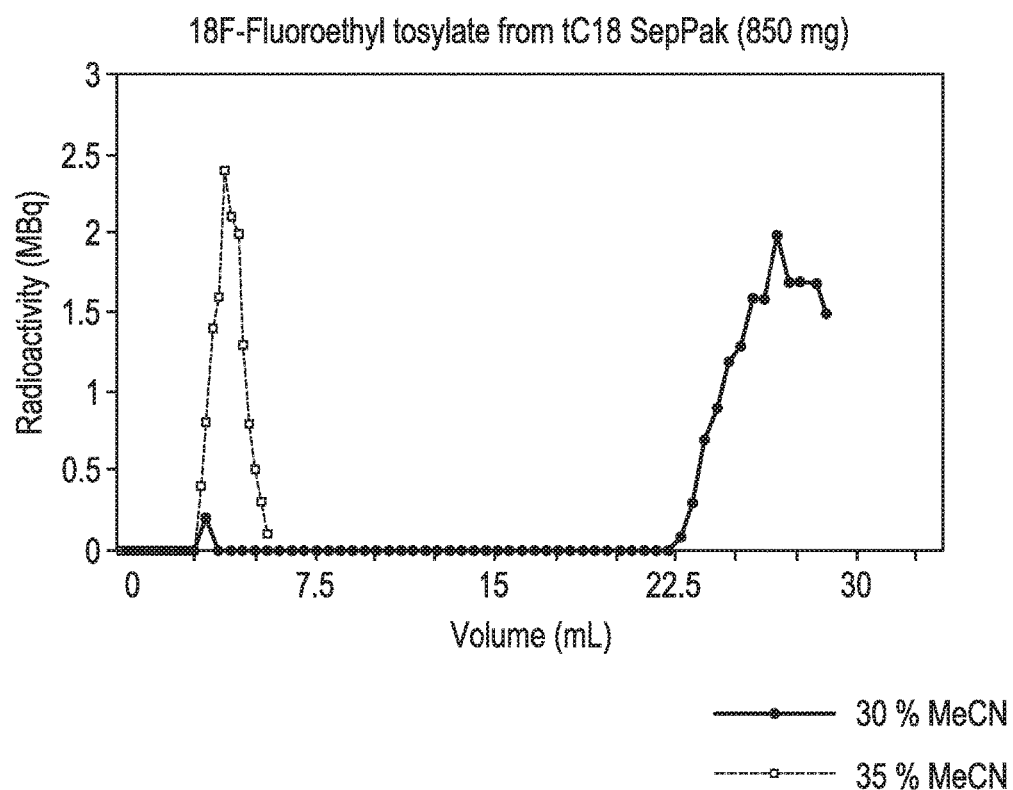
FIG. 3 Comparison of a tC18 cartridge performance after loading with a full FASTlab reaction volume containing crude 2 followed by manual elution.

The present invention provides a method of purifying [$^{18}$F]-fluoroalkyl tosylates using an automated radiosynthesis apparatus.

The present method provides a method of purifying [$^{18}$F]-fluoroalkyl tosylates using a FASTlab module that includes a solid phase extraction (SPE) purification system.

The present invention provides a method of purifying [$^{18}$F]2-fluoroethyl tosylate using an automated radiosynthesis apparatus.

The present method provides a method of purifying [$^{18}$F]2-fluoroethyl tosylate using a FASTlab module that includes a solid phase extraction (SPE) purification system.

According to the present invention, the [$^{18}$F]-fluoroalkyl tosylate can be any [$^{18}$F]-fluoroalkyl tosylate known in the art. In one embodiment, the [$^{18}$F]-fluoroalkyl tosylate is [18F]Fluoromethyl, [18F]-2-fluoroethyl, or [18F]-3-fluoropropyl tosylate (see e.g., Pascali, G., Mazzone, G., Saccomanni, G., Manera, C. & Salvadori, P. A. Microfluidic approach for fast labeling optimization and dose-on-demand implementation. *Nucl. Med. Biol.* 37, 547-555 (2010)).

In one embodiment, the [$^{18}$F]-fluoroalkyl tosylate is [18F] 3-Fluoropropyl tosylate (see e.g., Tang, G., Tang, X., Wang, M., Luo, L. & Gan, M. Fully automated synthesis of O-(3-[$^{18}$F]fluoropropyl)-L-tyrosine by direct nucleophilic exchange on a quaternary 4-aminopyridinium resin. *Appl. Rad. Isot.* 58, 685-689 (2003)).

In one embodiment, the [$^{18}$F]-fluoroalkyl tosylate is [18F] Fluoromethyl or [18F]-2-fluoroethyl tosylate (see e.g. Robins, E. G. et al. Synthesis and in vitro evaluation of 18F-labelled S-fluoroalkyl diarylguanidines: Novel high-affinity NMDA receptor antagonists for imaging with PET. *Bioorg. Med. Chem. Lett.* 20, 1749-1751 (2010)).

In one embodiment, the [$^{18}$F]-fluoroalkyl tosylate is [18F] Fluoromethyl tosylate (see e.g., Neal, T. R., Apana, S. & Berridge, M. S. Improved synthesis of [$^{18}$F]fluoromethyl tosylate, a convenient reagent for radiofluoromethylations. *J. lab. Comp. & Radiophann.* 48, 557-568 (2005)).

In one embodiment, the [$^{18}$F]-fluoroalkyl tosylate is [$^{18}$F] 2-fluoroethyl tosylate.

According to the present invention, the SPE purification system can be any SPE purification system known in the art. Examples of SPE systems include, but are not limited to, tC2, tC18, and C30 columns, including large tC2, large tC18, and C30 columns, using various eluents such as, but not limited to, acetonitrile and ethanol. According to the invention, flow and product monitoring can be achieved by an adapted radio HPLC system.

An [$^{18}$F]-fluoroalkyl tosylate, as described herein, can be prepared using methods known in the art. A more detailed discussion of well-known $^{18}$F labelling techniques can be found in Chapter 6 of the "Handbook of Radiopharmaceuticals" (2003; John Wiley and Sons: M. J. Welch and C. S. Redvanly, Eds.).

In one embodiment [$^{18}$F]2-fluoroethyl tosylate can be prepared from ditosylate 1 according to Scheme 1 below:

SCHEME 1

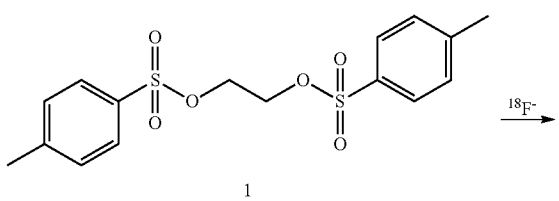

1

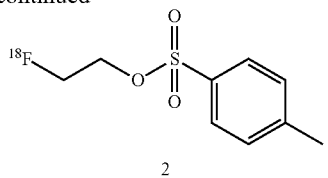

2

The radioisotope [$^{18}$F]-fluoride ion can be prepared by means known in the art. By way of example, the radioisotope [$^{18}$F]-fluoride ion ($^{18}$F$^-$) is normally obtained as an aqueous solution from the nuclear reaction $^{18}$O(p,n)$^{18}$F and is made reactive by the addition of a cationic counterion and the subsequent removal of water. Suitable cationic counterions should possess sufficient solubility within the anhydrous reaction solvent to maintain the solubility of 18F$^-$. Therefore, counterions that have been used include large but soft metal ions such as rubidium or caesium, potassium complexed with a cryptand such as Kryptofix™, or tetraalkylammonium salts. A preferred counterion is potassium complexed with a cryptand such as Kryptofix™ because of its good solubility in anhydrous solvents and enhanced $^{18}$F$^-$ reactivity.

Automated Radiosynthesis Apparatus

There are several commercially-available examples of such platform apparatus, including TRACERlab™ (e.g., TRACERlab™ MX) and FASTlab™ (both from GE Healthcare Ltd.). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. Optionally, in a further embodiment of the invention, the automated radiosynthesis apparatus can be linked to a high performance liquid chromatography (HPLC).

The present invention therefore provides a cassette for the automated synthesis of [$^{18}$F]2-fluoroethyl tosylate comprising:

(i) a vessel containing a crude reaction product comprising [$^{18}$F]2-fluoroethyl tosylate; and
(ii) an SPE cartridge.

According to the present invention, a cassette of the present invention may, optionally, further comprise one or more of the following:

(iv) a QMA cartridge;
(v) a QMA eluent; and/or
(ix) a line directed to an HPLC system.

Figure 4A:
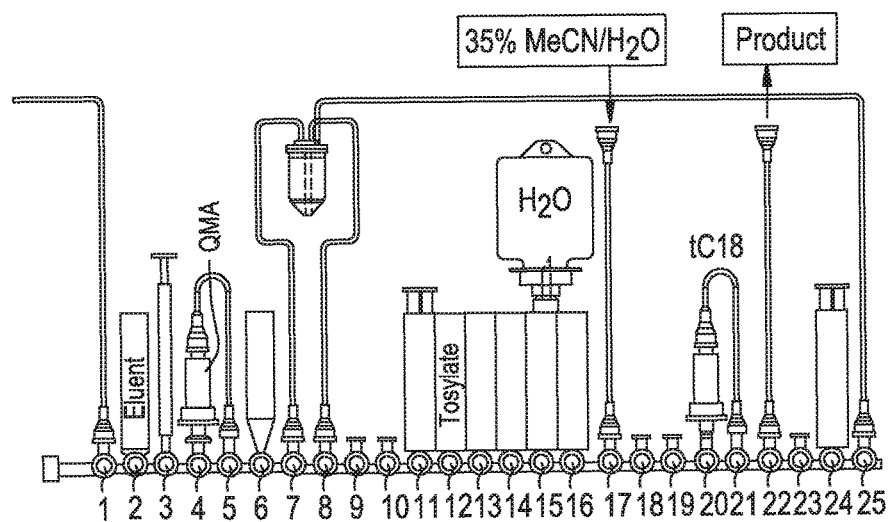
FIG. 4A FASTlab cassette layout.
Figure 4B:
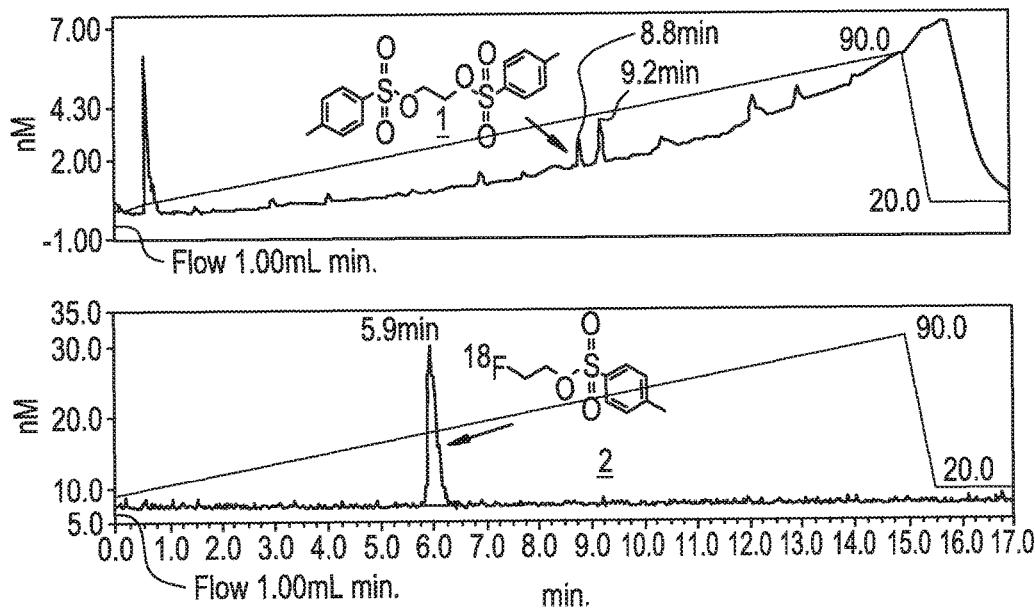
FIG. 4B HPLC analysis of tC18 purified product. The cartridge was eluted with 35% MeCN/H$_2$O (3 fractions of 6.6 mL).

In one embodiment, a cassette of the present invention is illustrated in FIG. 4.

Example 1

Methods:

A crude mixture of [$^{18}$F]2-fluoroethyl tosylate was produced by a FASTlab module. Purification of the [$^{18}$F]2-fluoroethyl tosylate was performed using alternative SPE systems (large tC2, large tC18, and C30) using acetonitrile and ethanol eluents. Flow and product monitoring was achieved by an adapted radio HPLC system.

Results:

There was no significant difference in the product/precursor separation efficiency between the tC2 and tC18 cartridges. The C30 cartridge showed only moderate peak resolution. Optimal isocratic tC18 cartridge elution of a full FASTlab reaction mixture was found for an eluent consisting of water/35% MeCN (v/v) giving a product recovery of 61% (corrected for decay) and a radiochemical purity of >99%.

Conclusion:

A large tC18 SepPak cartridge can be used for a FASTlab protocol to synthesize and purify [$^{18}$F]2-fluoroethyl tosylate.

What is claimed is:

1. A method of purifying crude [$^{18}$F]2-fluoroethyl tosylate using a positron-emission tomography (PET) tracer production platform that comprises a cassette-based chemical synthesizer and the cassette comprises fluid pathways, a reaction vessel, ports for receiving reagent vials as well as a solid phase extraction (SPE) cartridge, the method comprising, reacting ethylene ditosylate with a source of $^{18}$F- to form the crude [$^{18}$F]2-fluoroethyl tosylate using the chemical synthesizer; and purifying said crude [$^{18}$F]2-fluoroethyl tosylate with SPE on the SPE cartridge.

2. The method of claim 1, wherein the SPE cartridge is a tC18 column using acetonitrile eluents.

3. The method of claim 1, wherein the SPE cartridge is a tC2 column.

4. The method of claim 1, wherein the SPE cartridge is a C30 column.

5. A method of purifying crude [$^{18}$F]2-fluoroalkyl tosylate using a positron-emission tomography (PET) tracer production platform that comprises a cassette-based chemical synthesizer and the cassette comprises fluid pathways, a reaction vessel, ports for receiving reagent vials as well as a solid phase extraction (SPE) cartridge, the method comprising, purifying said crude [$^{18}$F]2-fluoroalkyl tosylate with SPE on the SPE cartridge.

6. The method of claim 5, wherein the SPE cartridge is a tC2 column.

7. The method of claim 5, wherein the SPE cartridge is a tC18 column.

8. The method of claim 5, wherein the SPE cartridge is a C30 column.

9. The method of claim 5, wherein the [$^{18}$F]2-fluoroalkyl tosylate is [$^{18}$F]2-fluoromethyl tosylate.

10. The method of claim 5, wherein the [$^{18}$F]2-fluoroalkyl tosylate is [$^{18}$F]2-fluoropropyl tosylate.

11. A method of purifying crude [$^{18}$F]2-fluoroethyl tosylate using a positron-emission tomography (PET) tracer production platform that comprises a cassette-based chemical synthesizer and the cassette comprises fluid pathways, a reaction vessel, ports for receiving reagent vials as well as a solid phase extraction (SPE) cartridge, the method comprising, purifying said crude [$^{18}$F]2-fluoroethyl tosylate with SPE on the SPE cartridge.

12. The method of claim 11, wherein the SPE cartridge is a tC2 column.

13. The method of claim 11, wherein the SPE cartridge is a tC18 column.

14. The method of claim 11, wherein the SPE cartridge is a C30 column.

* * * * *